(12) United States Patent
Perov et al.

(10) Patent No.: US 6,407,395 B1
(45) Date of Patent: Jun. 18, 2002

(54) PORTABLE BIOCHIP SCANNER DEVICE

(75) Inventors: Alexander Perov, Troitsk; Alexei Sharonov, Moscow, both of (RU); Andrei D. Mirzabekov, Darien, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/515,290

(22) Filed: Feb. 29, 2000

(51) Int. Cl.[7] ............................................. G01N 21/64
(52) U.S. Cl. ................................ 250/458.1; 250/459.1
(58) Field of Search ........................ 250/458.1, 459.1, 250/252.1; 356/326, 318, 451

(56) References Cited

U.S. PATENT DOCUMENTS

| 5,459,325 | A | | 10/1995 | Hueton et al. | |
|---|---|---|---|---|---|
| 5,528,050 | A | | 6/1996 | Miller et al. | |
| 5,631,734 | A | | 5/1997 | Stern et al. | |
| 5,991,030 | A | * | 11/1999 | Yamamoto et al. | ......... 356/346 |
| 6,078,390 | A | * | 6/2000 | Bengtsson | ................. 356/318 |
| 6,197,503 | B1 | * | 3/2001 | Vo-Dinh et al. | ............... 435/6 |

OTHER PUBLICATIONS

DNA analysis and diagnostics on oligonucleotide microchips, by Yershov G. et al, Proc. Natl. Acad. Sci. USA, vol. 93, pp. 4913–4918, May 1996.

* cited by examiner

*Primary Examiner*—Constantine Hannaher
*Assistant Examiner*—Otilia Gabor
(74) *Attorney, Agent, or Firm*—Joan Pennington

(57) ABSTRACT

A portable biochip scanner device used to detect and acquire fluorescence signal data from biological microchips (biochips) is provided. The portable biochip scanner device employs a laser for emitting an excitation beam. An optical fiber delivers the laser beam to a portable biochip scanner. A lens collimates the laser beam, the collimated laser beam is deflected by a dichroic mirror and focused by an objective lens onto a biochip. The fluorescence light from the biochip is collected and collimated by the objective lens. The fluorescence light is delivered to a photomultiplier tube (PMT) via an emission filter and a focusing lens. The focusing lens focuses the fluorescence light into a pinhole. A signal output of the PMT is processed and displayed.

16 Claims, 3 Drawing Sheets ably small, for example, a few hundred or even less.

PORTABLE BIOCHIP SCANNER DEVICE

CONTRACTUAL ORIGIN OF THE INVENTION

The United States Government has rights in this invention pursuant to Contract No. W-31-109-ENG-38 between the United States Department of Energy (DOE) and the University of Chicago representing Argonne National Laboratory.

FIELD OF THE INVENTION

The present invention relates to a portable biochip scanner device used to detect and acquire fluorescence signal data from biological microchips (biochips), in particular oligonucleotide biochips.

RELATED APPLICATION

A related U.S. Pat. No. 6,329,661, entitled "A BIOCHIP SCANNER DEVICE", by Alexander Perov, Alexander I. Belgovskiy and Andrei D. Mirzabekov is being filed on the same day as the present patent application.

DESCRIPTION OF THE RELATED ART

At the present time, biochips, after being incubated with a sample solution containing fluorescently labeled target molecules are assayed using either a microscope equipped with a charge coupled device (CCD) camera or a laser scanner. To acquire large volume of digital data (1–100 MB per image) in a reasonable time these devices employ sophisticated optical, mechanical, and electronic components which results in high cost of the hardware used. Regardless of the technique of fluorescence measurement used, all known biochip analyzers are high-resolution imaging instruments. This means that their output data is essentially a digital image of the chip composed of approximately 1000N elementary data points, where N represents the number of biochip immobilization sites. As a biochip user is typically interested in relative fluorescence intensities of the immobilization sites, an image as the output data format is highly redundant and requires further processing before the data can be analyzed. This may include signal integration over the immobilization sites, background subtraction, and normalization. The image processing is especially difficult in the case of analyzers based on wide-field microscopes, in which both the sensitivity and the image background are inherently non-uniform. With increasing complexity of biochips, the software for processing the fluorescence data becomes increasing intricate and rather demanding in terms of computer memory and processor speed.

The above identified related application discloses a novel technique of reading biochips that we refer to as Discrete Scanning (or Row Scanning) and a laser scanner that embodies this principle in practice. In contrast to the imaging scanners, this device scans exclusively the rows of a biochip array, the beam focal spot being adjusted to match the size of the array elements. The scanner employs a HeNe laser emitting at 594 nm to excite Texas Red-labeled target molecules, an optical system with a fiber-optic output for delivery of the excitation light to a miniature scanning head, and a low-noise photodiode as a fluorescence detector. A computer-controlled positioning system is used to move the scanning head in both X and Y directions to monitor the intensity of fluorescence for each element of a 2D biochip array. The above setup provides a detection threshold and dynamic range close to those of commercially available biochip readers. In the same time, it is much less demanding in terms of the amplifiers bandwidth, analog-to-digital conversion rate, optical resolution, and scanning mechanics parameters.

There is, however, a need for even simpler and portable biochip reader device. These requirements are typical for applications in which the number of biochip array elements sufficient to assure adequate analytical capability is relatively small, for example, a few hundred or even less.

SUMMARY OF THE INVENTION

A principal object of the present invention is to provide a portable biochip scanner device used to detect and acquire fluorescence signal data from biological microchips (biochips) and method of use. Other important objects of the present invention are to provide such method and portable biochip scanner device substantially without sacrificing the sensitivity and dynamic range; and to overcome some disadvantages of prior art arrangements.

In brief, a portable biochip scanner device used to detect and acquire fluorescence signal data from biological microchips (biochips) is provided. The portable biochip scanner device employs a laser for emitting an excitation beam. An optical fiber delivers the laser beam to a portable biochip scanner. A lens collimates the laser beam, the collimated laser beam is deflected by a dichroic mirror and focused by an objective lens onto a biochip. The fluorescence light from the biochip is collected and collimated by the objective lens. The fluorescence light is delivered to a photomultiplier tube (PMT) via an emission filter and a focusing lens. The focusing lens focuses the fluorescence light into a pinhole. A signal output of the PMT is processed and displayed.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
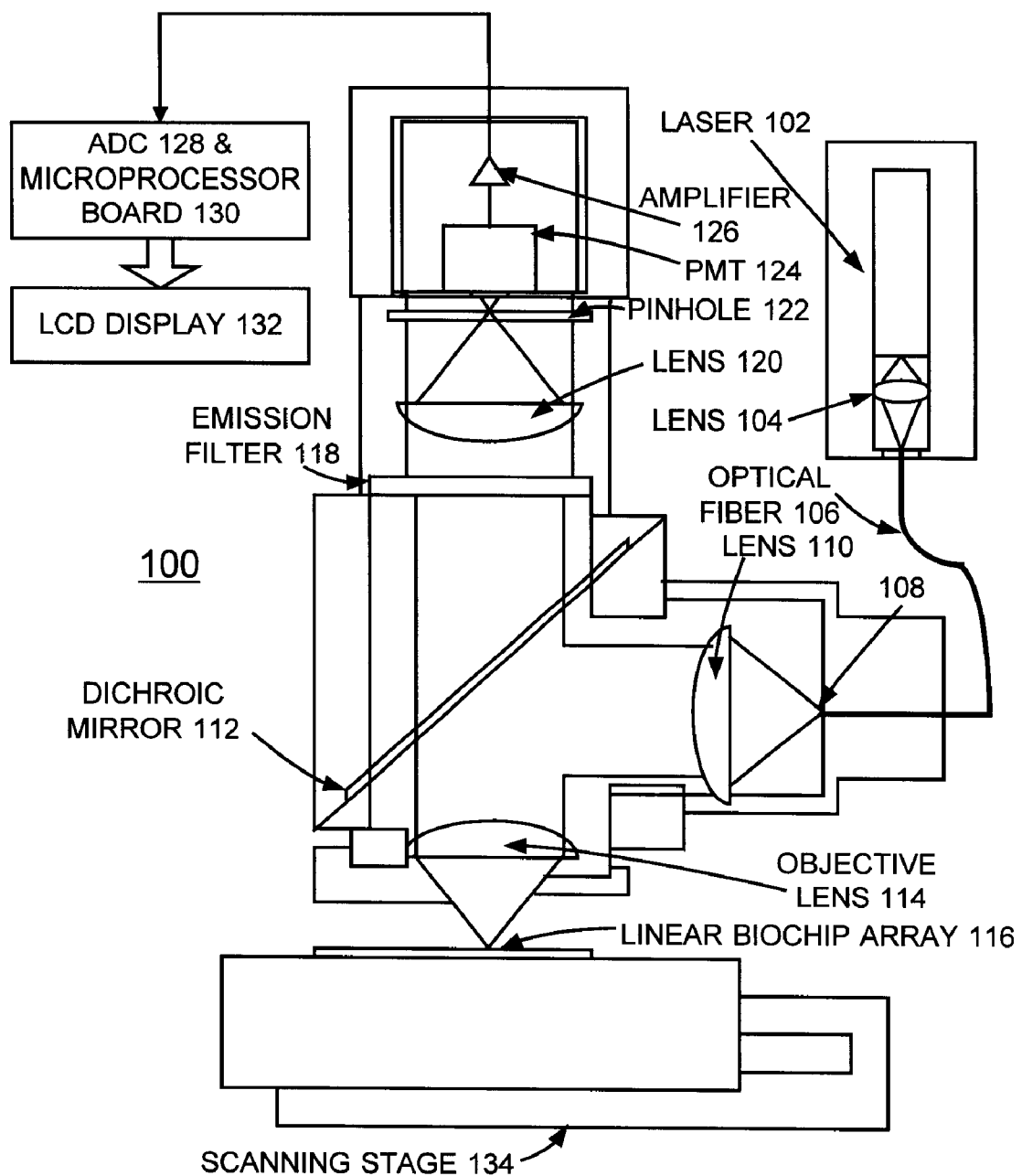
FIG. 1 is a schematic and block diagram illustrating a portable biochip scanner device in accordance with the preferred embodiment.

Having reference now to the drawings, in FIG. 1, there is shown a portable biochip scanner device in accordance with the preferred embodiment generally designated by the reference character 100. Portable biochip scanner device 100 is used to detect and acquire fluorescence signal data from biochips, such as oligonucleotide biochips.

In accordance with features of the invention, scanner 100 can include compact photodetectors, such as photodiodes or miniature photomultiplier tubes and low-power lasers and provide the performance characteristics necessary for reliable detection of fluorescence at the level of 100,000 fluorescent molecules/gel pad. Using the discrete scanning technique allows for considerably relaxed hardware characteristics, such as bandwidth, analog-to-digital conversion rate, optical resolution, and scanning mechanics parameters without sacrificing sensitivity and dynamic range of the instrument.

Portable biochip scanner device 100 is particularly effective for applications in which the number of biochip array elements required to assure adequate analytical capability is relatively small (few hundreds or even less), whereas low cost and portability of the reader device are highly desirable. The discrete portable biochip scanner device 100 is designed to meet these requirements.

Portable biochip scanner device 100 employs a compact solid-state laser 102 emitting at a wavelength matching the excitation band of a particular flurophore. In one embodiment, this laser 102 would be a 5 mW diode laser emitting at 635 nm, which falls close enough to the absorption maximums of such fluorescent labels as "Bodipy 650" and Cy5. Laser 102 also could be a frequency-doubled diode-pumped Nd:YAG laser emitting at 532 nm which suitable for exciting such labels as tetramethylrodamine, Cy3, and Lissamine.

Laser 102 operates in a continuous-wave mode. A lens 104 focuses the laser beam into an optical fiber 106 which delivers the light to a filter compartment 108. Here, a lens 110 collimates the beam. The collimated beam is next deflected by a dichroic mirror 112 and focused by an objective lens 114 onto the biochip 116 mounted on a scanning stage 134. The ratio of the focal lengths of the lenses 110 and 114 is chosen to have the beam diameter on the biochip equal to the size of the biochip array elements. The fluorescence light emerging from the biochip array elements is collected and collimated by the lens 114. Then the light passes in sequence the dichroic mirror 112, an emission interference filter 118 and a lens 120 which focuses the fluorescence light into a pinhole 122. The pinhole 122 rejects the stray light that otherwise would contribute to the background. A photomultiplier tube (PMT) 124 serves as a light detector. In the embodiment described here the photomultiplier is an integral part of a miniature detector module that also includes a high-voltage power supply for the PMT and a transimpedance amplifier 126 that converts the signal photocurrent into voltage. Such photomultiplier detector modules are commercially available, for example from Hamamatsu Corp. of Bridgewater, N.J. Next, the signal is digitized with an analog-to-digital converter (ADC) 128 and processed by a microprocessor board 130. The processing may include digital filtering and integration of the signal. The microprocessor can also be used as a driver of a compact liquid-crystal display (LCD) 132 employed for monitoring the scanner output.

In practical use, the operator initiates a scan by sending an appropriate signal, for example by pressing a button on the instrument's front panel to the controller of scanning stage 134. When the scanning stage 134 arrives in a certain position designated as a "Start Scan" position, a position sensor located close to the stage sends a signal to the microprocessor board 130 that controls the data acquisition and the ADC 128 starts periodical sampling of the PMT amplifier output. On the stage arrival at a second, "End Scan", position, another position sensor stops the data acquisition in a similar manner. The digital data obtained is processed and displayed on the LCD screen 132, for instance, as a bar diagram, each bar representing the integral fluorescence intensity of a particular biochip array element.

A lens part number C220-TM-B sold by Thorlabs of Newton, N.J. can be used for the first lens 110. A lens part number C230-TM-B sold by Thorlabs of Newton, N.J. can be used for the objective lens 114. A lens part number C220-TM-B sold by Thorlabs of Newton, N.J. can be used for lens 104 and lens 120. For 635 nm excitation wavelength, a diode laser module part number DLM 3604-635 sold by Optima Precision of West Linn, Oreg., can be used as laser 102, and a filter part number 670DF40 and a dichroic mirror part number 640DRLP, both sold by Omega Optical of Brattleboro, Vt. can serve as emission filter 118 and dichroic mirror 112, respectively.

For 532 nm excitation wavelength, a diode pumped solid state laser part number BR-LPC-3-X sold by Brimrose of Baltimore, Md., can be used as laser 102, and a filter part number 565EFLP and a dichroic mirror part number 670DRLP, both sold by Omega Optical of Brattleboro, Vt. can serve as emission filter 118 and dichroic mirror 112, respectively.

Pinhole 122 can be implemented with a part number 04 PPM 017 sold by Melles Griot of Irvine, Calif. The ADC 128 can be implemented with a data acquisition card number LabPC 1200 sold by National Instruments of Austin, Tex. The scanning mechanics 126 can be implemented with a linear scanning stage part number 402002LN-MP-DL3CRM1 sold by Daedal of Harrison City, Pa.

Figure 2A:
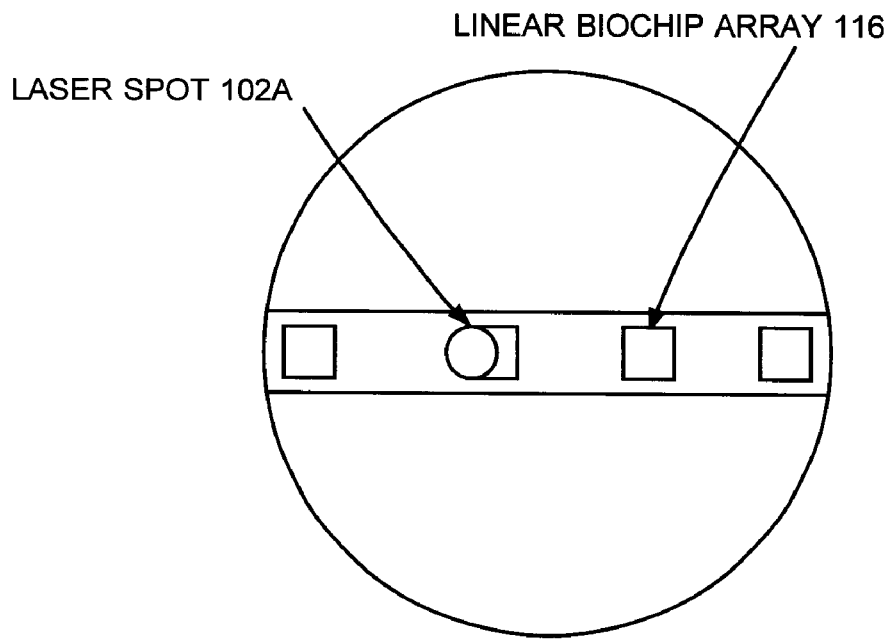
FIGS. 2A and 2B are diagrams illustrating a linear biochip array in accordance with the preferred embodiment.
Figure 2B:
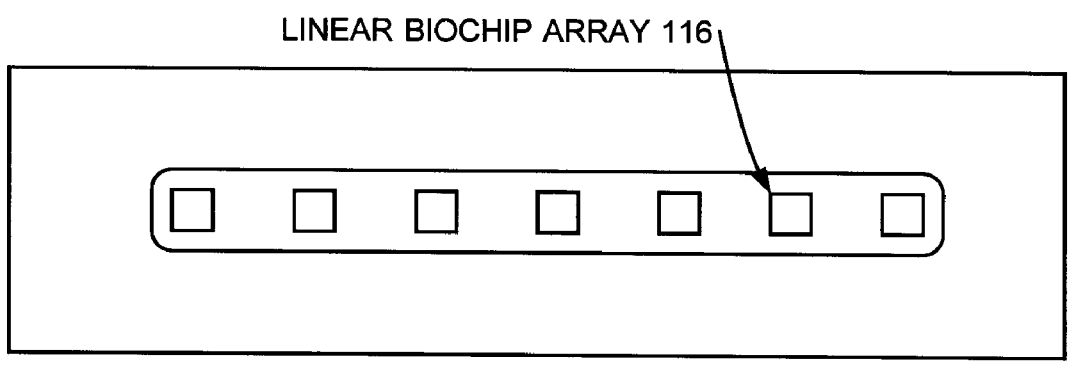

FIGS. 2A and 2B are diagrams illustrating a linear biochip array in accordance with the preferred embodiment. Referring to FIG. 2A, the size of a laser beam spot 102A substantially matches the immobilization site of the linear biochip array 116. FIG. 2B illustrates the linear biochip array 116.

Figure 3:
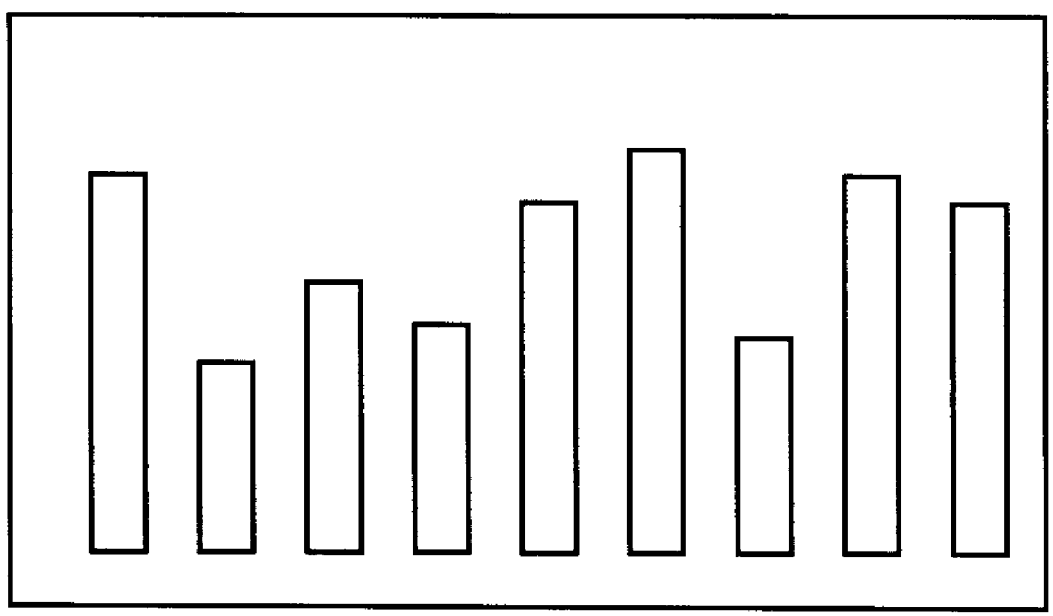
FIG. 3 is a diagram illustrating a LCD display of the portable biochip scanner device in accordance with the preferred embodiment.

FIG. 3 illustrates an exemplary display on the LCD display 132 of the portable biochip scanner device 100 in accordance with the preferred embodiment. As shown, as a bar diagram, each bar represents the integral fluorescence intensity of a particular element of biochip array 116.

What is claimed is:

1. A portable biochip scanner device, said portable biochip scanner device for quantifying a plurality of linear arrays of substantially separated, dimensionally uniform fluorescent targets, said arrays located at known positions on a plain support of a biochip; said portable biochip scanner device comprising:

a laser for emitting a laser beam of excitation radiation;

a first lens for collimating said laser beam of excitation radiation;

a dichroic mirror for deflecting said collimated laser beam of excitation radiation;

an objective lens for focusing said laser beam of excitation radiation into a focal spot onto the biochip; said focal spot having a selected size substantially equal to a size of said substantially separated, dimensionally uniform fluorescent targets and for collecting and collimating fluorescence light of each said illuminated fluorescent target from the biochip;

means for delivering said fluorescence light of each said illuminated fluorescent target to a detector, said detector providing a signal output; and means for processing and displaying said signal output of said detector.

2. A portable biochip scanner device as recited in claim 1 includes a scanning stage coupled to said biochip for moving said biochip relative to the portable biochip scanner for directing said laser beam focal spot for sequentially illuminating said fluorescent targets one at a time and for sequentially collecting fluorescence light of each said illuminated fluorescent target.

3. A portable biochip scanner device as recited in claim 1 wherein said means for delivering said fluorescence light to said detector include an emission filter and a focusing lens.

4. A portable biochip scanner device as recited in claim 3 wherein said focusing lens is for focusing said fluorescence light into a pinhole.

5. A portable biochip scanner device as recited in claim 3 wherein said emission filter is for receiving and filtering said fluorescence light of each said illuminated fluorescent target from the biochip.

6. A portable biochip scanner device as recited in claim 5 wherein said detector includes a photomultiplier tube (PMT) for detecting said filtered fluorescence light of each said illuminated fluorescent target and providing said signal output.

7. A portable biochip scanner device as recited in claim 6 wherein said photomultiplier tube (PMT) includes a transimpedance amplifier for converting a signal photocurrent into voltage.

8. A portable biochip scanner device as recited in claim 1 wherein said means for processing and displaying said signal output of said detector includes an analog-to-digital converter (ADC).

9. A portable biochip scanner device as recited in claim 8 includes a microprocessor board.

10. A portable biochip scanner device as recited in claim 9 includes a liquid crystal display.

11. A portable biochip scanner device as recited in claim 1 wherein said laser includes one of a red or infrared diode laser.

12. A portable biochip scanner device as recited in claim 1 includes an optical fiber for delivering said laser beam of excitation radiation to said first lens.

13. A portable biochip scanner device, said portable biochip scanner device for quantifying a plurality of linear arrays of substantially separated, dimensionally uniform fluorescent targets, said arrays located at known positions on a plain support of a biochip; said portable biochip scanner device comprising:

a laser for emitting a laser beam of excitation radiation;

a first lens for collimating said laser beam of excitation radiation;

a dichroic mirror for deflecting said collimated laser beam of excitation radiation;

an objective lens for focusing said laser beam of excitation radiation into a focal spot onto the biochip; said focal spot having a selected size substantially equal to a size of said substantially separated, dimensionally uniform fluorescent targets and for collecting and collimating fluorescence light of each said illuminated fluorescent target from the biochip;

said dichroic mirror for delivering said fluorescence light to an emission filter for receiving and filtering said fluorescence light of each said illuminated fluorescent target from the biochip;

a focusing lens for focusing said fluorescence light of each said illuminated fluorescent target into a pinhole;

a detector for detecting said filtered fluorescence light and providing a signal output; and means for processing and displaying said signal output of said detector.

14. A portable biochip scanner device as recited in claim 13 wherein said means for processing and displaying said signal output of said detector includes an analog-to-digital converter (ADC), a microprocessor board and a liquid crystal display.

15. A portable biochip scanner device as recited in claim 13 includes an optical fiber for delivering said laser beam of excitation radiation to said first lens.

16. A portable biochip scanner device as recited in claim 13 wherein said detector comprises a photomultiplier tube (PMT).

* * * * *